US012053275B1

(12) United States Patent
Ryan

(10) Patent No.: US 12,053,275 B1
(45) Date of Patent: Aug. 6, 2024

(54) APPARATUS FOR MONITORING RESPIRATORY RATE, VOLUMES AND DRIVE PATTERNS

(71) Applicant: Steven Bruce Ryan, Ames, IA (US)

(72) Inventor: Steven Bruce Ryan, Ames, IA (US)

( * ) Notice: Subject to any disclaimer, the term of this patent is extended or adjusted under 35 U.S.C. 154(b) by 587 days.

(21) Appl. No.: 17/330,016

(22) Filed: May 25, 2021

(51) Int. Cl.
*A61B 5/00* (2006.01)
*A61B 5/08* (2006.01)
*A61B 5/091* (2006.01)
*A61B 5/113* (2006.01)
*G01B 7/24* (2006.01)
*G01B 11/16* (2006.01)

(52) U.S. Cl.
CPC .......... *A61B 5/1135* (2013.01); *A61B 5/0806* (2013.01); *A61B 5/0816* (2013.01); *A61B 5/091* (2013.01); *A61B 5/6823* (2013.01); *A61B 5/6831* (2013.01); *G01B 7/24* (2013.01); *G01B 11/16* (2013.01)

(58) Field of Classification Search
CPC ... A61B 5/1135; A61B 5/0806; A61B 5/0816; A61B 5/091; A61B 5/6823; A61B 5/6831; G01B 7/24; G01B 11/16
See application file for complete search history.

(56) References Cited

U.S. PATENT DOCUMENTS

| | | |
|---|---|---|
| 3,731,184 A | 5/1973 | Goldberg et al. |
| 4,308,872 A | 1/1982 | Watson et al. |
| 4,846,462 A * | 7/1989 | Regnier ............. A63B 23/0244 600/595 |
| 5,191,893 A * | 3/1993 | Reiten .................. A61B 5/4818 600/595 |
| 5,522,401 A * | 6/1996 | Brucker ............. A63B 23/0244 482/148 |
| 5,857,984 A * | 1/1999 | deBoer .............. A63B 23/0244 600/595 |
| 6,551,252 B2 | 4/2003 | Sackner et al. |

(Continued)

OTHER PUBLICATIONS

Augousti, Maletras and Mason, "Improved fibre optic respiratory monitoring using a figure-of-eight coil," Physiological Measurement, 2005, 26 (5), 585-590.

(Continued)

*Primary Examiner* — Steven O Douglas
(74) *Attorney, Agent, or Firm* — BrownWinick Law Firm; Christopher A. Proskey

(57) ABSTRACT

A device and method for monitoring respiration in freely moving subjects uses measurement of changes in axial circumference during respiration to compute, store, and display respiratory rate, volume flows, and drive patterns. Since the embodiments allow a direct absolute measure of circumference throughout the respiratory cycle, they are amenable to low frequency sampling and provide an opportunity to use anthropometric scaling without resorting to concomitant spirometry. Belt sensors arranged in parallel to belt tautening forces permit independent adjustment of preload forces on the displacement-measuring components. The monitoring system can be used at home to facilitate a wide range of health and fitness objectives such as tracking dysfunctional breathing patterns, optimizing athletic training, and learning relaxation practices such a pranayama.

20 Claims, 7 Drawing Sheets

(56) References Cited

U.S. PATENT DOCUMENTS

| | | | | |
|---|---|---|---|---|
| 7,967,760 B2* | 6/2011 | Lang | ............ | A61B 5/6823 |
| | | | | 600/534 |
| 8,790,274 B2 | 7/2014 | McCool | | |
| 9,801,583 B2 | 10/2017 | Derchak et al. | | |
| 10,182,727 B2 | 1/2019 | Gargiulo et al. | | |
| 10,393,497 B2 | 8/2019 | Park et al. | | |
| 2015/0342518 A1* | 12/2015 | Persidsky | ............ | A61B 5/6831 |
| | | | | 600/534 |

OTHER PUBLICATIONS

Binks, et al., "An inexpensive, MRI compatible device to measure tidal volume from chest-wall circumference," Physiological Measurement, 2007, 28(2), 149-159.

Leutheuser et al. "Reference-Free Adjustment of Respiratory Inductance Plethysmography for Measurements during Physical Exercise," IEEE Trans Bio-Med Eng. 2017, 64(12), 2836-.

Martinot-Lagarde et al., "What does inductance plethysmography really measure?" Journal of Applied Physiology, 1988, 64(4), 1749-1756. American Physiological Society.

* cited by examiner

APPARATUS FOR MONITORING RESPIRATORY RATE, VOLUMES AND DRIVE PATTERNS

TECHNICAL FIELD

The present disclosure relates to methods and devices for monitoring respiration in freely moving subjects, specifically measuring changes in thoracic and abdominal circumferences throughout the respiratory cycle for use in calculating and analyzing respiratory rate, volumes and drive patterns.

BACKGROUND

Monitoring respiration in the home promises to be invaluable for a wide variety of health and fitness objectives. Disturbances in breathing during sleep, for instance, manifest in or exacerbate many disorders such as congestive heart failure, chronic obstructive pulmonary disease, and sleep apneas. Dysfunctional breathing patterns, such as those seen in postural orthostatic tachycardia syndrome and possibly in long-lasting respiratory effects of mild covid-19 infection, may lend themselves to modification by training methods that utilize awareness of rate, volumes, and drive source (thoracic vs. abdominal breathing). Furthermore, in healthy individuals, ambulatory respiratory monitoring can serve to facilitate athletic training, sleep tracking, and also relaxation practices such as pranayama.

Pulmonary function monitoring in the clinical setting has traditionally used direct measurement of volume flows into and out of either the lungs (spirometry, flow spirometry) or an enclosure surrounding the body (body plethysmography). Since spirometry and flow spirometry require the use of mouthpieces or masks, which interfere with normal respiration, disrupt mobility and sleep, and since body plethysmography requires a large, expensive enclosure, these techniques are not well suited to track respiratory function in ambulatory subjects at home.

Many methods can extract respiratory rate or make qualitative assessments of respiratory volumes in ambulatory subjects, for example arterial photoplethysmography (U.S. Pat. No. 10,098,550 Al-Ali and Majmudar 2018), or single transect measures of thoracic or abdominal circumference (U.S. Pat. No. 10,765,345 Kang et al. 2020, U.S. Pat. No. 10,595,779 Laugstol 2020). Accurate estimation of volume flows and identification of patterns of thoracic and abdominal contributions to respiration, however, require independent measures of abdominal and rib cage dimensions throughout the respiratory cycle.

Prior methods for ambulatory monitoring of pulmonary function via abdominal and thoracic dimensions include measuring: the self-inductance of sinusoidally arranged wires within circumferential elastic bands (U.S. Pat. No. 3,731,184 Goldberg and Goldberg 1973, U.S. Pat. No. 4,308,872 Watson et al. 1982, U.S. Pat. No. 6,551,252 Sackner and Inman 2003), the magnetic flux across paired transmit and receive coil magnetometers (U.S. Pat. No. 8,790,274 McCool 2014, U.S. Pat. No. 9,801,583 Derchak et al. 2017), the strain-induced resistance changes in conductive polymers (U.S. Pat. No. 10,182,727 Gargiulo and Breen 2019), the macro-bending loss effect in optical fibers (Augousti, Maletras and Mason, 2005, "Improved fibre optic respiratory monitoring using a figure-of-eight coil," Physiological Measurement, 2005, 26 (5), 585-590), and the pressure changes inside flexible corrugated chambers stretched between belts encircling the body in an axial plane (Binks, et al. 2007, "An inexpensive, MRI compatible device to measure tidal volume from chest-wall circumference," Physiological Measurement, 2007, 28(2), 149-159). Unfortunately, resistance changes in conductive threads or polymers are not linearly related to displacement. Additionally, strain-based belt systems locate the sensors in series with the baseline tension required to keep the belt in place so that this tension is part of the signal, potentially reducing the dynamic range available for measuring the stretch induced by respiration.

Previous work in respiratory plethysmography, including that utilizing inductance and magnetometer devices, has developed methods for weighting and summing separate signals from rib-cage and abdominal geometries to produce estimates of breath volumes normalized to the vital capacity (maximal breath volume, volume moved by a maximal exhale after a maximal inhale) of the subject. Conversion of normalized volumes to absolute volumes, however, requires at least one session of concomitant spirometry. An ideal respiration monitor would not need this kind of calibration device but would instead use anthropometric data such as transverse cross-sectional area or circumference to scale the output to volume. Sophisticated modeling indicates that anthropometric scaling is feasible and that rib cage and abdominal circumferences are important parameters to consider (Leutheuser et al. "Reference-Free Adjustment of Respiratory Inductance Plethysmography for Measurements during Physical Exercise," IEEE Transactions on Bio-medical Engineering, 2017, 64(12), 2836-2846).

In theory, respiratory inductance plethysmography lends itself to absolute measures of transverse dimensions, since the inductance of a planar wire loop is a function of the enclosed cross-sectional area. Practical use of this effect to measure respiration, however, requires that the wire be arranged in a sinusoidal or triangular wave shape within an elastic band in order to accommodate changing dimensions. When such a band is stretched during inspiration, geometrical distortion of the wave shape directly affects the inductance, thereby limiting its use as an absolute measure of area (Martinot-Lagarde et al., "What does inductance plethysmography really measure?" Journal of Applied Physiology, 1988, 64(4), 1749-1756)

In other technical arenas, previous use of magnetic encoders to measure distance (U.S. Pat. No. 10,393,497 Park et al. 2019) did not envision measurement of dynamically changing body circumference and so did not arrange a parallel belt tightening force or capability for continuous monitoring of a changing dimension.

SUMMARY OF THE EMBODIMENTS

The disclosed embodiments are directed toward monitoring respiratory rate, volume flows, and drive patterns in freely moving subjects through measurement of changes in rib cage and abdominal circumference during respiration. The embodiments measure circumferential displacements with sensors arranged in parallel to belt tautening forces and then use these displacements to compute parameters such as breath rate, normalized volume, and drive patterns. Displacements and computed parameters can be stored and communicated to a computer or smartphone for analysis. Furthermore, the embodiments allow a direct absolute measure of axial circumference throughout the respiratory cycle, providing an opportunity to use anthropometric scaling for determining absolute volume flows without resorting to spirometery. The present embodiments are easily optimized for battery application, do not require inductor loop drive currents needed for both inductance and magnetometer systems, and can spent most of a sampling cycle in low power sleep mode. Thus, the embodiments represent a convenient and efficient way to track respiratory function in non-clinical settings.

BRIEF DESCRIPTION OF THE DRAWINGS

The following figures illustrate embodiments of the respiratory monitoring device.

DETAILED DESCRIPTION OF SPECIFIC EMBODIMENTS

Figure 1:
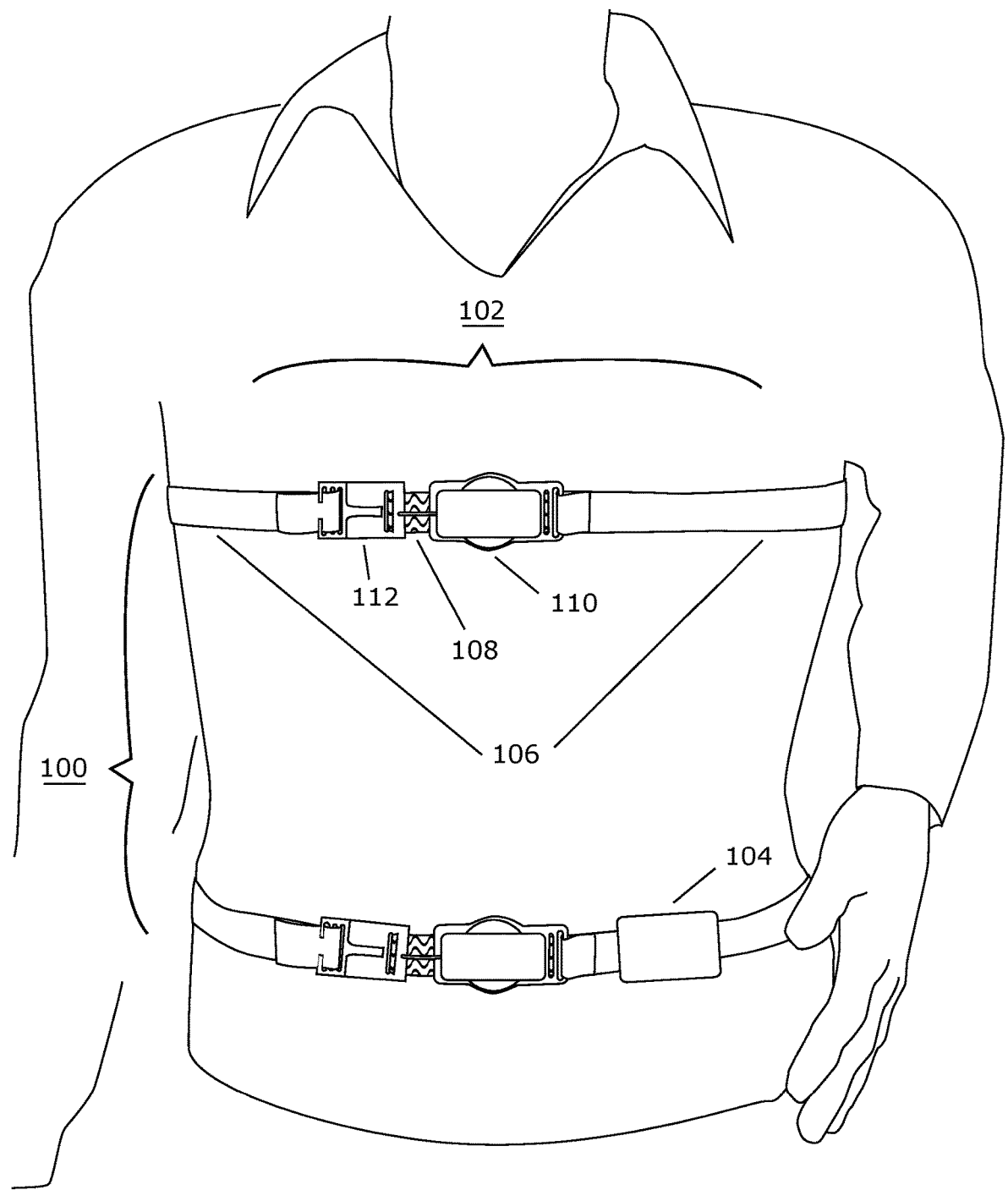
FIG. 1 shows the front view of one embodiment of the device with two sensors wrapped about a torso.

FIG. 1 illustrates one embodiment of a respiratory monitoring device 100. In this embodiment, the device 100 comprises two body circumference sensors 102 and a microprocessor system 104. Each circumference sensor 102 includes: an inelastic belt 106, which is wrapped around a torso and held taut against the torso by a tautening part, and a displacement-measuring part 110. In this embodiment, an elastic band 108 is used as the tautening part but other embodiments might use other methods to accomplish tautening, a spring, for example. A buckle 112 is disposed to join a first end of the inelastic belt 106 to a first end of the elastic band 108 in order facilitate placement and removal of the sensor 102.

Body Circumference Sensors

Figure 2:
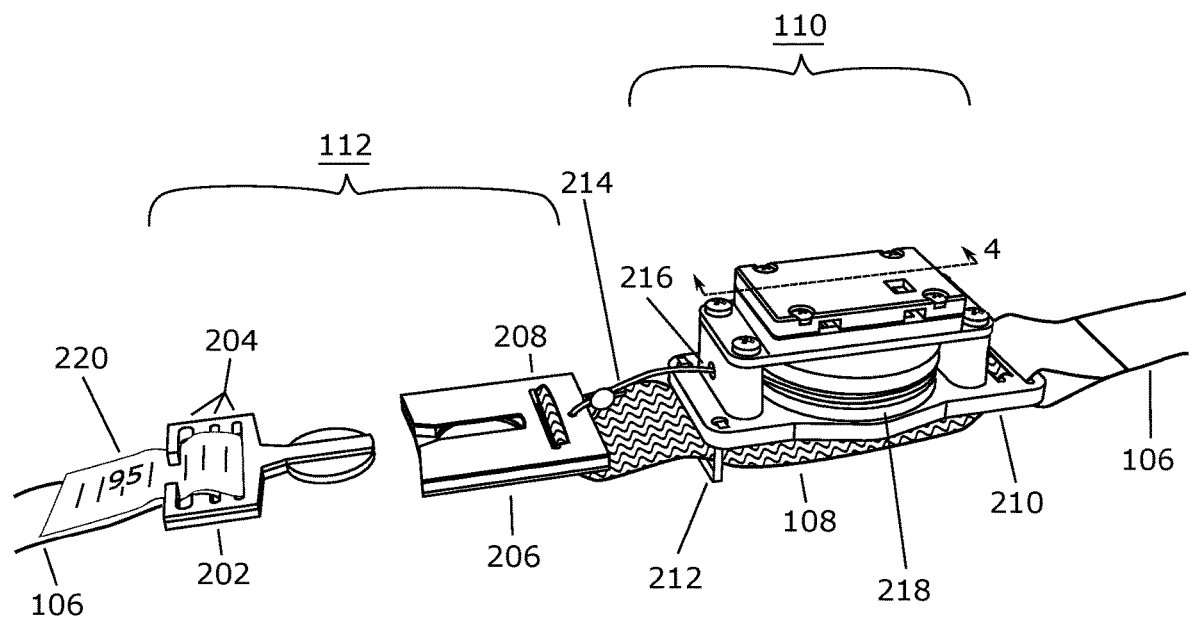
FIG. 2 shows a close view of a displacement-measuring part and its adjustable attachment to a buckle at one end of an elastic band and its fixed attachment at one end of an inelastic belt.

FIG. 2 shows in more detail another embodiment of the displacement-measuring part 110 and its connections to the inelastic belt 106, the elastic band 108, and the buckle 112. The buckle 112 consists of two interlocking parts, a male part 202 with slots 204 for connecting and adjusting the length of the first end of the inelastic belt 106, a female part 206 with a slot 208 for connecting the first end of the elastic band 108. In this embodiment, a second end of the elastic band 108 and a second end of the inelastic belt 106 both connect to the first end of the displacement-measuring part 110, specifically to a base 210 of the displacement-measuring part 110. Although this embodiment shows the inelastic belt 106 and the elastic band 108 connecting independently to the base 210, other arrangements are envisioned, such as a direct connection between the inelastic belt 106 and the elastic band 108 with a second direct connection between the base 210 and the inelastic belt 106.

The displacement-measuring part 110 is disposed to overlie a portion of the elastic band 108 by its connection to the second end of the elastic band 108 and by an alignment guide 212 which maintains the position of the base 210 while allowing the elastic band 108 to slide through and stretch. Thus, tautening forces generated by pulling the first end of the inelastic belt 106 through the slots 204 of the buckle 112 are directed through the buckle 112, to the elastic band 108, to the second end of the inelastic belt 106.

A flexible attachment, illustrated in this embodiment as a string 214, is slidably attached at its first end to the female part 206 of the buckle 112, is passed through a guidance hole 216 in the base 210, is wound about a spool 218, and is attached to the spool 218 at its second end. The spool 218 has a rotational elastic element arranged to return the spool back to its original orientation after any rotation. Thus, any movement of the buckle 112 away from the base 210 and away from the second end of the inelastic belt 106 pulls on the string 214, causing the spool 218 to rotate and the force of the rotational elastic element to increase. This force retracts the string 214 when the buckle 112 moves back toward the base and toward the second end of the inelastic belt 106. As illustrated in detail below, rotation of the spool 218 is detected by rotary encoders located within the displacement-measuring part.

Rule marks 220 on the inelastic belt 106 allow the user to note the set length of the belt; this dimension can be used to convert relative displacement data to absolute circumference measurements.

Figure 3:
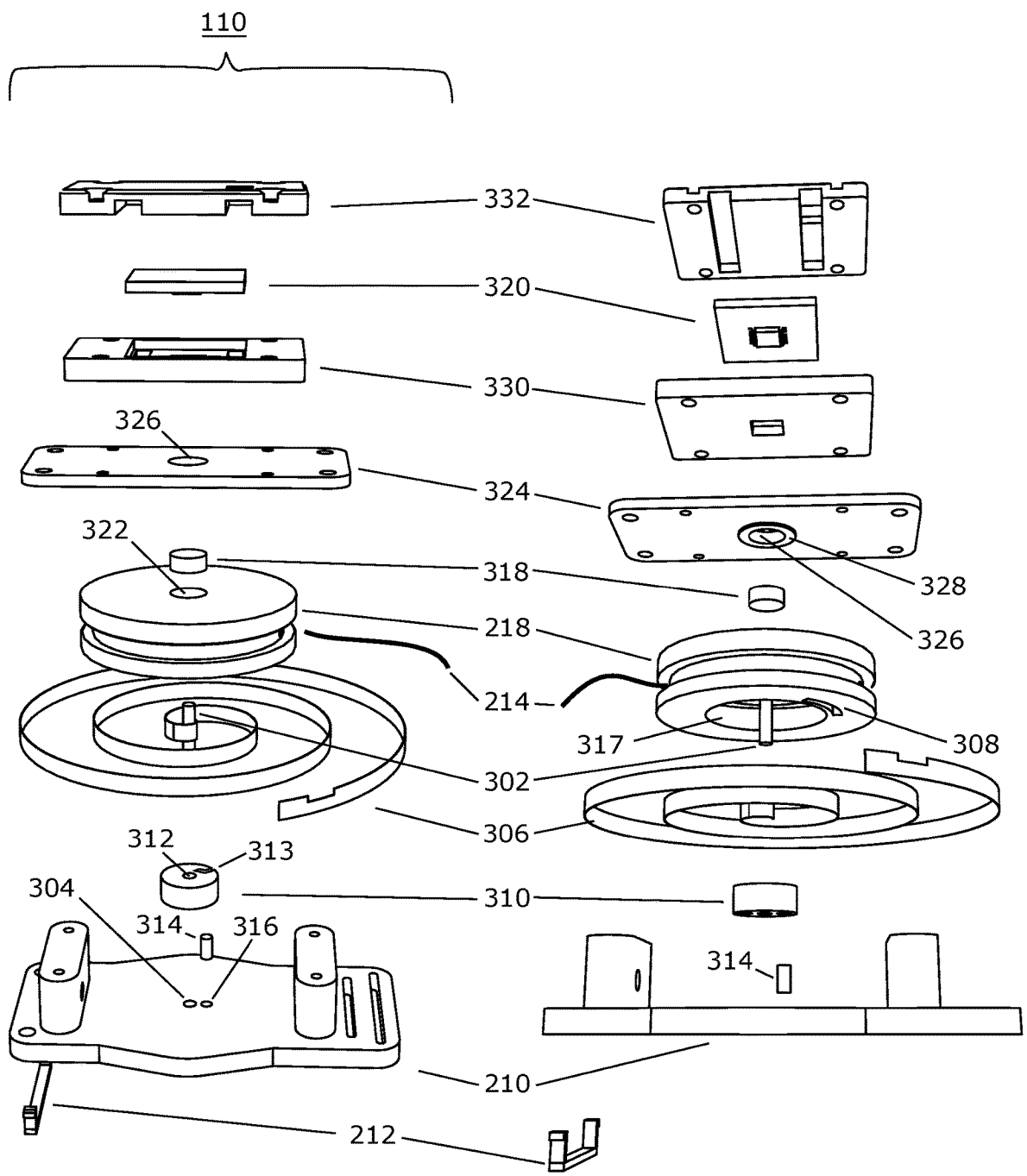
FIG. 3 shows an exploded view of one embodiment of a displacement-measuring part in two orientations to better see underlying parts.

FIG. 3 shows a disassembled view of one embodiment of the displacement-measuring part 110 in two orientations. In this embodiment, rotation is detected by use of magnetic encoders but another embodiment could use a different physical means for measuring rotation such as an optical means. The detailed description provided herein is meant to illustrate one method for measuring rotation but should not be construed as limiting the method to magnetic means only.

In one embodiment, the spool 218 has an axle 302 fixed at its first end on the cylindrical axis of the spool 218. A second end of the axle 302 rests in an axle bearing hole 304 in the base 210 such that the spool 218 can rotate freely with respect to the base 210. In this embodiment, the rotational elastic element is a spiral torsion spring 306 which is connected at its first end to the spool 218 via a spool spring anchor slot 308. A second end of the spiral torsion spring 306 is connected to the base 210 through a base spring anchor 310. The base spring anchor 310 includes axle clearance hole 312 to accommodate the axle 302 such that the axle rotates freely in the clearance hole, and a base spring anchor slot 313 that connects to the second end of the torsion spring 306. The base spring anchor 310 also has a hole to accommodate a first end of a registration pin 314. The base 210 has a registration pin hole 316 to accommodate a second end of the registration pin 314 such that the pin prevents rotation of the base spring anchor 310 with respect to the base 210 when the spool 218 is turned and the torsion spring 306 transmits force to the base spring anchor 310. In this embodiment, the base spring anchor 310 and the spiral torsion spring 306, when assembled, are located within a cavity 317 of the spool as shown in section view in FIG. 4.

In order to monitor rotation of the spool 218, a magnet 318 is fixed to the cylindrical axis of the spool 218 and a magnetic encoder 320 is positioned over the magnet 318, such that the magnetic field of the magnet 318 is detectable in the magnetic encoder 320. The magnet 318 is fixed in a magnet mount hole 322 located on the cylindrical axis of the spool 218 opposite to the axle 302 such that the axle 302 and the magnet 318 are aligned on the cylindrical axis of the spool 218. This arrangement allows the magnet 318 to serve as a second bearing surface, permitting the spool 218 to rotate smoothly on its cylindrical axis. A magnetic bearing plate 324 is fixably attached to the base 210 and has a magnetic bearing hole 326 that permits the free rotation of the magnet 318. The magnetic bearing plate 324 also has a bearing annulus 328 which reduces surface contact between the spool 218 and the bearing plate 324. The magnetic encoder 320 is affixed to the magnetic bearing plate 324 between an encoder mount plate 330 and an encoder cover 332.

In this embodiment, the alignment guide 212, simply snaps into the base 210, and allows free passage of the elastic band beneath the base 210 while maintaining the position of the base 210 over the elastic band.

Figure 4:
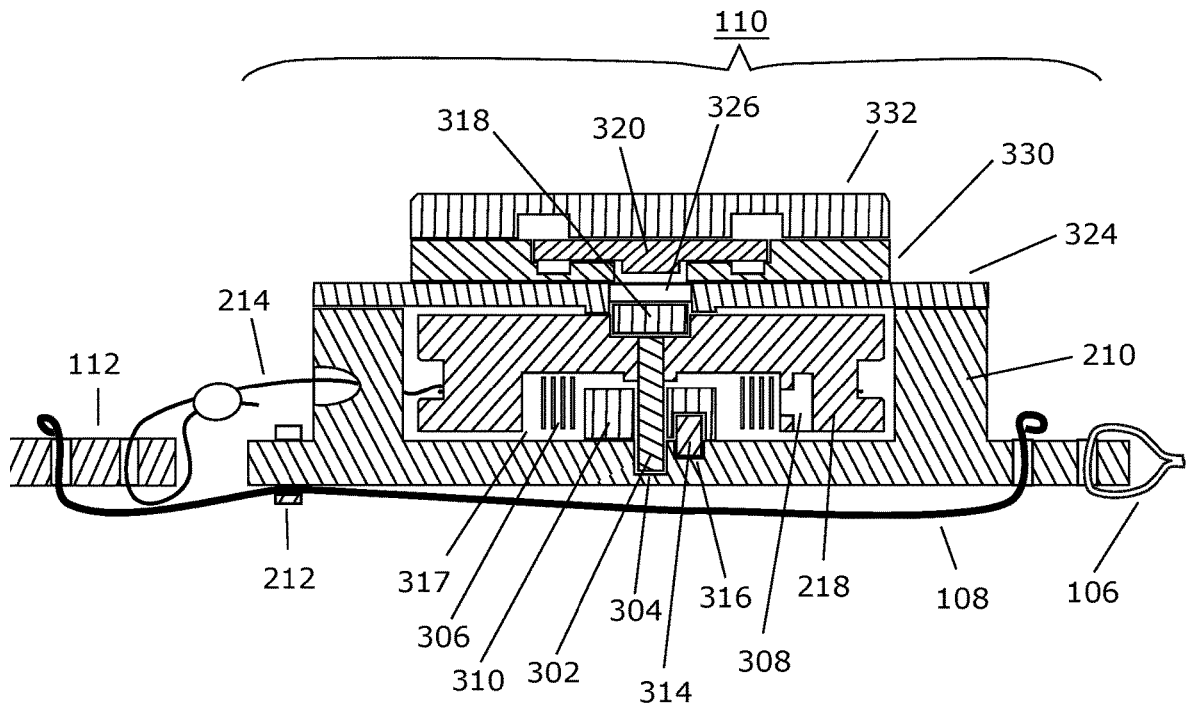
FIG. 4 shows a section view of another embodiment of a displacement-measuring part; section line is indicated in FIG. 2.

FIG. 4 shows a section view of one embodiment of the assembled displacement-measuring part 110. The line of section and view direction are indicated 4 in FIG. 2. As described previously, the spool 218 rotates with respect to the base 210 around an axis formed by the axle 302 and the magnet 318. Both the axle 302 and the magnet 318 are affixed to the spool 218. Holes 304, 326 in the base 210 and the magnetic bearing plate 324, respectively, form bearing surfaces for the axis. The spiral torsion spring 306 and the base spring anchor 310 are located in the spring cavity 317 of the spool 218. The registration pin 314 prevents rotation of the base spring anchor 310 with respect to the base 210. The magnetic encoder 320 is aligned with the cylindrical axis of the spool 218 and is held in place with the encoder mount plate 330 and the encoder cover 332. The entire encoder subassembly, comprising the magnetic encoder 320, the encoder mount plate 330, and the encoder cover 332 are affixed to the magnetic bearing plate 324. The connections of the displacement-measuring part 110 to the inelastic belt 106, the elastic band 108, and the buckle 112 are also shown in FIG. 4. A first end of the base 210 connects to the inelastic belt 106 and also to the elastic band 108. The alignment guide 212 is attached to a second end of the base 210 such that the elastic band 108 can slide freely through. Thus, tautening forces used to maintain the position of the body circumference sensor on the torso of the subject are primarily directed through the second end of the inelastic belt 106, through the first end of the base 210, though the elastic band 108, through the buckle 112, to the first end of the inelastic belt.

Since the string 214 of the displacement-measuring part 110 is slidably attached to the buckle 112, preload forces directed through the string 214 to the spool 218 to the spiral torsion spring 306 are adjustable independently of baseline tautening forces in the inelastic belt 106.

An increase in torso circumference, caused by respiratory movements, pulls the two ends of the inelastic belt 106 apart. Since the base 210 is connected to the second end of the inelastic belt 106 and the string 214 is connected through the buckle 112 to the first end of the inelastic belt 106, this increase in circumference pulls the string 214 and causes the spool 218 to rotate. Rotation of the spool 218 and the attached magnet 318 with respect to the magnetic encoder 320 is detected by the encoder 320 and communicated to the microprocessor system.

Figure 5:
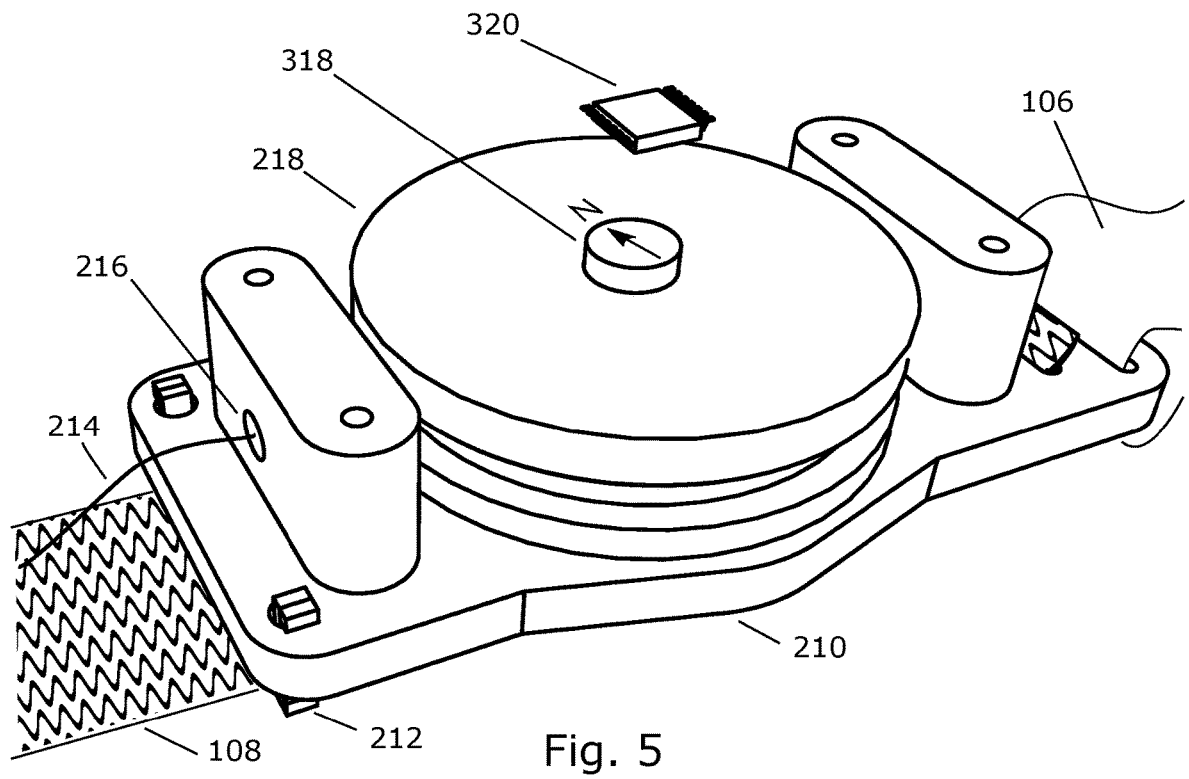
FIG. 5 shows magnetic components of an embodiment of a displacement-measuring part along with a base, spool, and elastic band; support structures are not shown so as to illustrate the relationship between a magnetic encoder and a magnet affixed to the spool that rotates when respiratory motions pull on a string.

FIG. 5 illustrates the orientation of the magnetic field, perpendicular to the cylindrical axis of the magnet 318 with respect to the magnetic encoder 320. In this view, the magnetic bearing plate, the encoder mount plate, the encoder cover, and the circuit board for the encoder have been removed to better show the orientations of the magnetic encoder 320 and the magnet 318. Respiratory movements pull on the string 214, causing the spool 218 and attached magnet 318 to rotate. Rotation of the magnetic field with respect to the magnetic encoder 320 is detected by the encoder and communicated to the microprocessor system.

Microprocessor System

Figure 6:
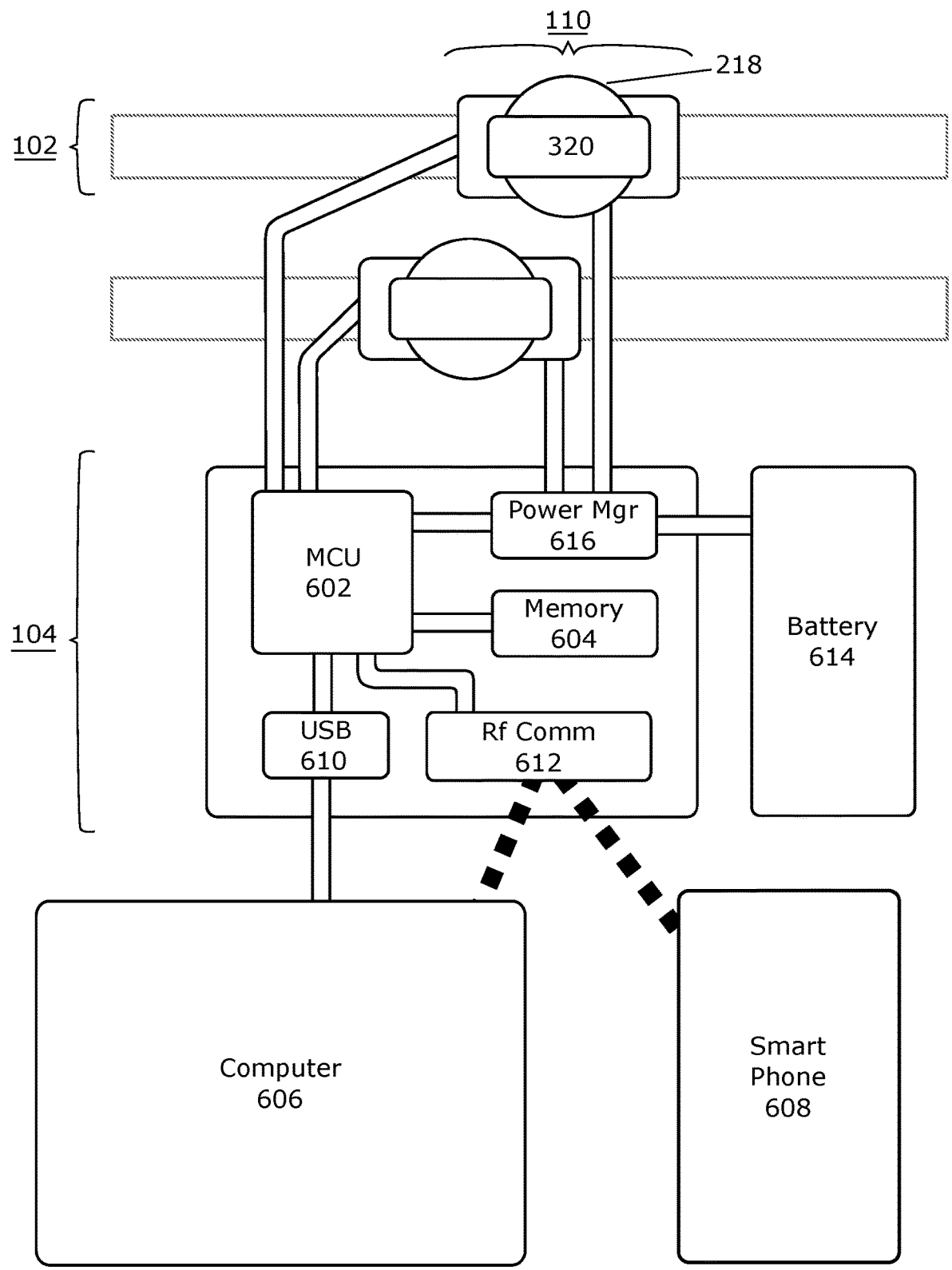
FIG. 6 is a schematic of the connections between a microprocessor system, the encoders and external devices such as a computer or smart phone.

Signal acquisition and processing by one embodiment of the microprocessor system 104 is illustrated in FIG. 6. In this embodiment, a microcontroller 602 manages the functions of the microprocessor system 104. The other components shown in the microprocessor system 104 are drawn as individual units to facilitate explanation of signal acquisition and processing. This separation should not be construed as limiting them to a location external to the microcontroller 602. In any embodiment, some of these components can be contained within the hardware of the microcontroller 602. Another embodiment might use external components to perform some or all of the functions described.

The microcontroller 602 communicates with the body circumference sensors 102, triggers the encoders 320 within the displacement-measuring part 110 to acquire rotation data, and stores the data in memory 604. As described above, the memory 604 could be located within the microcontroller 602 or could be external to the microcontroller in the form of random access memory or flash memory, as is standard in the art of embedded systems. The microcontroller 602 also manages communication with a general purpose computer 606 or a smart phone 608 for display and analysis of data from the displacement-measuring part 110. This communication could be in the form of a wired connection, such as USB 610 or through radio connections 612.

In some embodiments, the microcontroller 602 performs calculations to convert rotation to displacement prior to storage in memory 604. In other embodiments, the microcontroller 602 converts rotation data to displacement after storage, but prior to communication with the general purpose computer 606 or with the smartphone 608. In still other embodiments, only rotation data is communicated to the computer 606 or smartphone 608; conversion of rotation data to displacement is then performed by the computer 606 or smartphone 608.

Since the respiratory monitoring device is designed for use by ambulatory subjects, the microprocessor system 104 and the displacement-measuring part 110 derive their power from a battery 614. The microcontroller 602 manages its own power use as well as that of the displacement-measuring parts 110. In some embodiments, power management by microcontroller 602 consists of using timed sleep states as is common in the art of embedded systems. Additionally other embodiments could include an external power management device 616 to remove power from the displacement-measuring part 110 during the timed sleep states, thus conserving the battery.

Power management is also affected by characteristics of the rotary encoder 320. In some embodiments, the encoder 320 within the displacement-measuring part 110 only measures incremental changes in rotary position of the spool 218. To track these incremental changes, the microcontroller 602 must query the encoder 320 at a relatively high frequency in order to avoid missing the largest increment. Thus the time available for sleep states is reduced. In other embodiments, however, the encoder 320 measures the absolute rotary position of the spool 218 and so permits a relatively low frequency communication with the microcontroller 602 and leaves more time available for sleep states.

Although FIG. 6 shows one microprocessor system 104 communicating with both displacement-measuring parts 110 through wired connections, another embodiment could include one microprocessor system 104 for each displacement-measuring part 110. Each microprocessor system could communicate with the general purpose computer 606 or smartphone 608, as described above. Furthermore, the two microprocessor systems could communicate with each other, such that the first microprocessor system communicates data from the first displacement-measuring part 110 to the second microprocessor system 104. This second microprocessor system then would manage all storage and calculations for both displacement-measuring parts 110.

Figure 7:
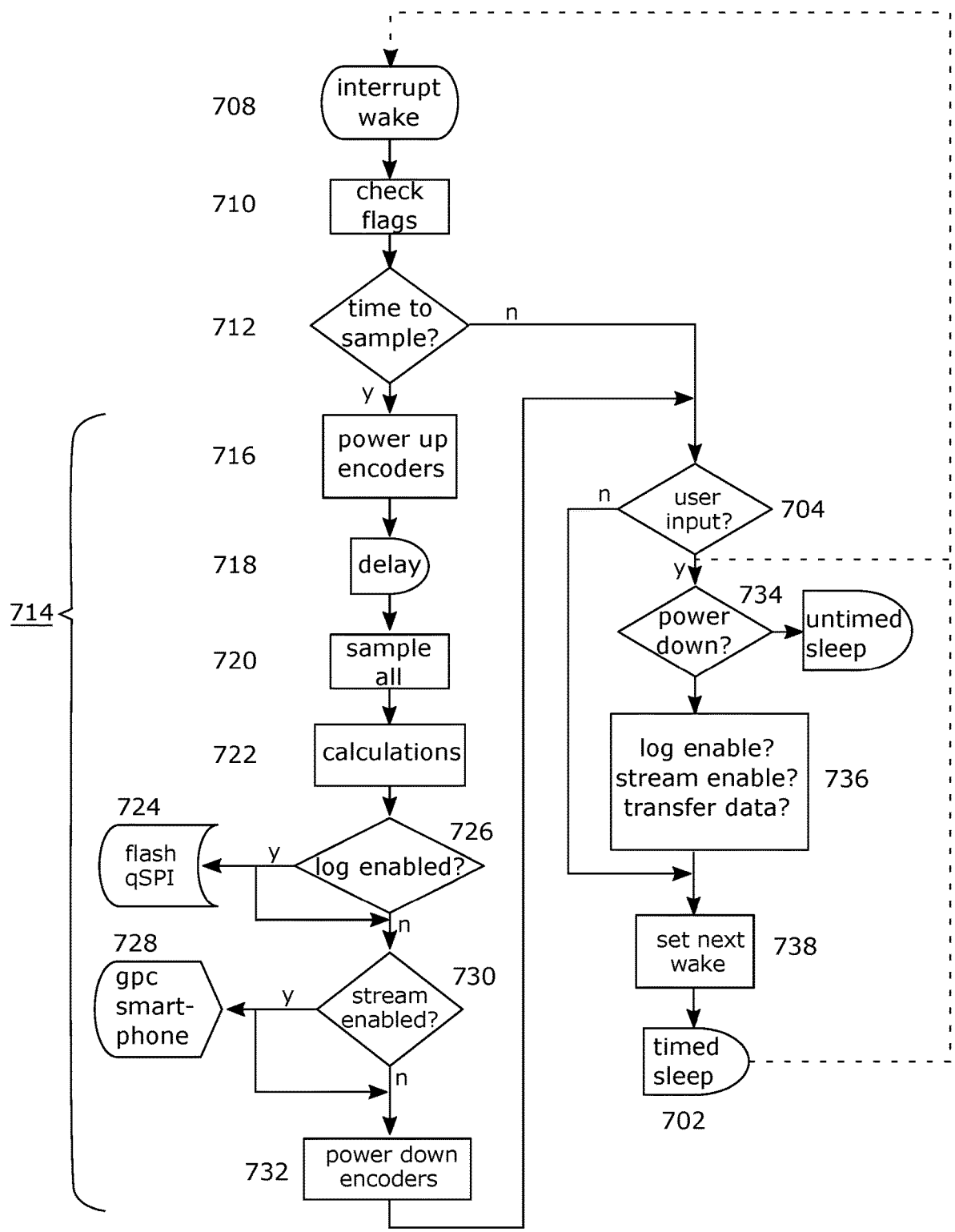
FIG. 7 shows a flow chart for measuring, storing, and communicating respiratory measurements.

FIG. 7 shows an exemplary flowchart for interrupt-driven processing in one embodiment of the microprocessor system. Interrupt events are illustrated with a dashed line. To conserve power and extend the life of the battery, the microprocessor suspends most operations and enters a low power sleep state 702 that can monitor interrupts generated by internal and external events. External events, such as a user pressing a button 704, or internal events, such as expiration of a predetermined time interval in an internal timer, trigger the microcontroller to exit the low-power sleep state and start a processing loop. Upon waking 708, the microcontroller first determines the source or sources of the interrupt by checking interrupt flags 710. If a timer interrupt has occurred, signaling that it is time to take another measurement 712, the microcontroller can initiate a sampling sequence 714.

In this embodiment, the encoders tracking rotation of the spool in the displacement-measuring part encode absolute angular position. This permits a complete shutdown of the encoder during low-power sleep as long as the timer wake interval is less than the time required for one half rotation at maximal speed. Since the diameter d of the spool determines the length of string displacement required to turn the spool one complete turn: $\pi*d$, and since this diameter is sized to approximate the displacement of a single breath, sampling frequency is constrained by Nyquist anti-aliasing considerations, in contrast to sampling frequency constraints imposed by the angular resolution of an incremental encoder.

Given the encoder shutdown, the initial step in the sampling sequence is to power up the encoders 716. A delay 718 permits the sensing circuitry within the encoders to stabilize and allows the microcontroller to initialize communication with the encoders. The encoders then sample rotation 720. After sampling, some embodiments could use rotation data from the encoders to calculate respiratory volumes 722, as described above. Alternatively, calculation of respiratory volumes could be done at a later time, such as during or after transfer of the data to the general purpose computer or smartphone. Sampled displacement data or calculated volumes could then be stored in memory 724, either within the microcontroller itself or in external memory such as static RAM or flash memory, contingent upon a log enable flag 726 set by the user. Additionally, displacement data or volumes could be live-streamed to an external viewing device 728, again contingent on a user setting 730. The sampling sequence 714 then terminates by shutting down power to the encoders 732.

Prior to returning a timed low power sleep state 702, the microcontroller checks for user requests 704 to enter an untimed low-power state 734, to change settings or to transfer stored data 736. The microcontroller then sets a timer 738 and enters low power sleep 702.

Calibration and Exemplary Recordings

Figure 8:
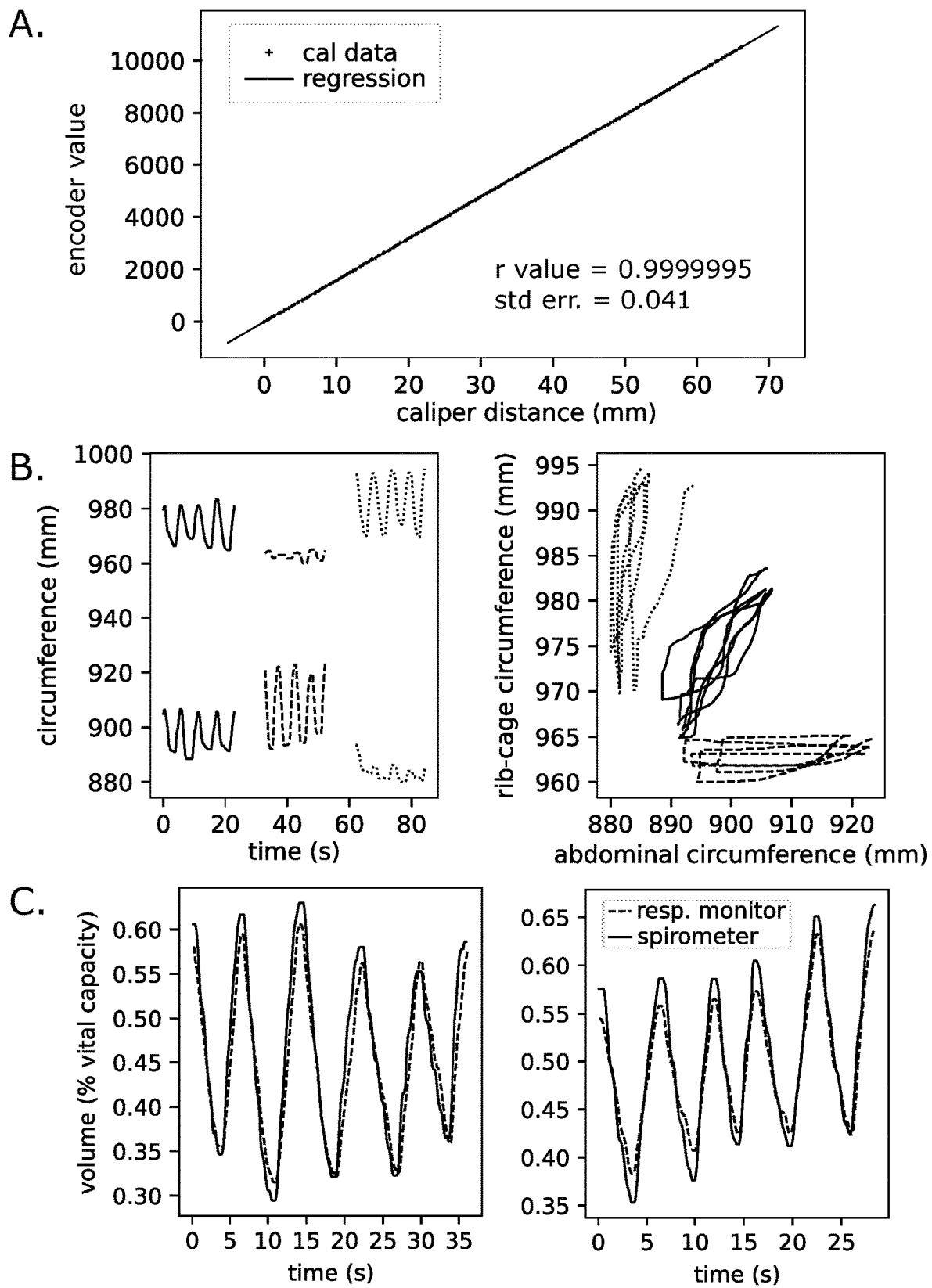
FIG. 8 shows calibration data for displacement measurement, exemplary recordings of respiratory circumferences during intentional alteration of drive patterns, and a comparison of the respiratory volumes calculated by one embodiment to volumes measured directly by spirometery.

Calibration of the encoder output from angular units to the corresponding distance is shown in FIG. 8A. To calibrate the output, the base of the displacement-measuring part was mounted to an aluminum bar and the string of the displacement-measuring part was connected to a slide block. A feed-screw between the base and the slide controlled the distance between them. This distance was measured with digital calipers and compared to the encoder output, plotted as crosses in FIG. 8A. A linear regression was then computed, plotted as a line in FIG. 8A. Slope and intercept from the regression were used to convert all encoder outputs to millimeters.

To track circumference during respiration, the constant lengths of the inelastic belts, as determined by rule marks on the belt, were added to displacements measured by the encoders. Thus, the respiratory monitoring device can measure body circumference at transects defined by the position of the belts, traditionally at the axilla and the umbilicus. The left panel of FIG. 8B shows exemplary recordings from the respiratory monitoring device for three separate trials. Top traces represent body circumference measurements at the axilla or 'rib-cage'. Bottom traces show circumference at the umbilicus or 'abdomen'. In the first trial (solid lines at left), the subject was breathing normally. The subject was then instructed to focus attention on breathing from the abdomen (dashed lines at center), and then from the chest (dotted lines at right).

Comparison of the abdominal vs the rib-cage circumference during these trials, FIG. 8B, right panel, shows distinct patterns for each trial. An inhalation driven from balanced displacements of the rib-cage and abdomen would appear as a line sloping upward and to the right, an exhalation, downward and to the left. In practice, however, inhalations and exhalations do not necessarily follow a single linear path, but rather circumscribe curvilinear loops. In this subject, such loops predominate in normal breathing (solid line). Emphasis on chest breathing (dotted lines) shifts the abdominal vs rib-cage circumference plot to a more vertical orientation, whereas emphasis on abdominal breathing (dashed lines) shifts it toward a more horizontal orientation. During quiet waking states, the abdominal vs rib-cage respiratory drive can shift subtly without conscious awareness and change dramatically during exercise, sleep, and mediation. Since tracking respiratory drive source is important for some forms of training and treatment, the respiratory monitoring device will have modes for immediate feedback, a sound or visual display on the smartphone for instance, and for off-line analysis.

In addition to assessing the rib-cage and abdominal contributions to respiration, transect measures of the thorax and abdomen can be combined to estimate respiratory volume flows. FIG. 8C shows a comparison of this estimation (dashed line) with a direct measurement of breath volumes using a Collins spirometer (solid lines) for two sessions of quiet breathing. Circumference displacements were first normalized by dividing them by the maximal displacement, given by a vital capacity maneuver, and then summed by a constant weighting factor of 2:1 for rib-cage: abdominal displacements (see Banzett et al., "A simple and reliable method to calibrate respiratory magnetometers and Respitrace," Journal of Applied Physiology, 1995, 79 (6), 2169-2176). No scaling factor was applied to the summed displacements. Although this simple calibration method produced good approximations of normalized breath volumes, further development of calibration techniques for the new respiratory monitoring device will certainly give better results, including anthropometric scaling factors for estimating absolute volumes.

The invention claimed is:

1. An apparatus for monitoring respiratory rates, volumes, and drive patterns comprising:
    a plurality of sensors configured to sense changes in body circumference, wherein each of the plurality of sensors includes:
    an inelastic belt having a first end and a second end;
        wherein the inelastic belt is wrapped about the circumference of a torso;
    a tautening elastic means having a first end and a second end;
        wherein the tautening elastic means is configured to connect the first end and the second end of the inelastic belt and maintain it taut against the torso during respiratory movements;
        wherein the tautening elastic means is configured to provide a tautening force;
    a displacement-measuring part disposed to overlie said tautening elastic means and to attach between the first end and the second end of the inelastic belt such that changes in the distance between the first end and the second end of said inelastic belt register in said displacement-measuring part;
        wherein most of the tautening force is exerted through an elastic means, parallel to a force urging movement of the displacement-measuring part;
    a microprocessor system configured to acquire displacement measurements at a predetermined rate.

2. The apparatus of claim 1 wherein said tautening elastic means is an elastic stretch band made of rubber or silicone.

3. The apparatus of claim 1 wherein said microprocessor system acquires body circumference changes from the plurality of sensors and communicates the body circumference changes to a general purpose computer or a smartphone at said predetermined rate.

4. The apparatus of claim 1 wherein said microprocessor system acquires body circumference changes from the plurality of sensors at said predetermined rate, stores the body circumference changes and communicates the body circumference changes at a later time to a general purpose computer or smartphone via a wired or wireless connection.

5. The apparatus of claim 1 wherein a buckle of two interlocking parts is disposed to join the first end of said inelastic belt to the first end of said tautening elastic means in order to facilitate placement and removal of a one of the plurality of sensors.

6. The apparatus of claim 1 wherein said microprocessor system acquires body circumference changes and computes any or all of the following data: respiratory volumes, respiratory frequency, respiratory volume flow, and respiratory drive patterns.

7. The apparatus of claim 6 wherein said microprocessor system communicates said data to a general purpose computer or a smartphone.

8. The apparatus of claim 6 wherein said microprocessor system stores said data, and communicates said data at a later time to a general purpose computer or smartphone via a wired or wireless connection.

9. The apparatus of claim 1 wherein said displacement-measuring part comprises:
    a spool having a cylindrical axis;
    a flexible attachment means slidably attached at a first end to the first end of said inelastic belt, wound about said spool, and attached at a second end to said spool,
    a base connected to the second end of said inelastic belt;
    a rotational elastic means to connect said base to said spool;
    a rotary encoder affixed to said base such that an increase in distance between the first end and the second end of said inelastic belt pulls on said flexible attachment means, causing said flexible attachment means to unwind from said spool and causing said spool to rotate and said rotary encoder to detect the rotation,
        wherein a decrease in distance between the first end and the second end of said inelastic belt allows said rotational elastic means to rotate said spool and wind said flexible attachment means about the spool, causing said rotary encoder to detect the rotation.

10. The displacement-measuring part of claim 9
    wherein a magnet is attached to the cylindrical axis of said spool;
    wherein said rotary encoder is a magnetic encoder disposed to overlie said magnet;
    wherein displacements of the first end and the second end of said inelastic belt cause said spool and said magnet to rotate and cause the magnetic encoder to detect the rotation.

11. The displacement-measuring part of claim 9 wherein said rotary encoder is an optical encoder.

12. The displacement-measuring part of claim 9 wherein said flexible attachment means is a string.

13. The displacement-measuring part of claim 9 wherein said flexible attachment means is a flat and flexible material such as a tape or band.

14. The displacement-measuring part of claim 9 wherein said rotational elastic means is a torsion spring such as a spiral or coil spring.

15. The displacement-measuring part of claim 9 wherein said rotational elastic means is a helical spring.

16. A method of monitoring respiratory function, the method comprising:
    arranging a plurality of sensors around the circumference of a torso, wherein each of the plurality of sensors comprises:
    an adjustable length of inelastic belt;
        wherein the inelastic belt has a first end and a second end;
    an elastic tautening means providing tautening force between the first end and the second end of said inelastic belt;
    and a displacement-measuring part disposed to connect the first end and the second end of said inelastic belt, in parallel to said elastic tautening means such that force on said displacement-measuring part can be adjusted independently of the tautening force of said elastic tautening means;
    using a microprocessor system to communicate with said plurality of sensors to detect and measure respiratory movements.

17. The method of claim 16 wherein said microprocessor system:

computes respiratory parameters such as breath volume, breath rate, volume flow and drive patterns;

stores said respiratory parameters in memory of said microprocessor system or in other memory media connected to said microprocessor system;

communicates said respiratory parameters, via wired or wireless connection, to a general purpose computer or smartphone for display, further analysis, and storage.

18. The method of claim 16 wherein said displacement-measuring part uses a string slidably attached to the first end of said inelastic belt to translate changes in circumference of the torso to rotation of a spool.

19. The method of claim 18 wherein said displacement-measuring part uses a magnetic encoder to sense rotation of said spool.

20. The method of claim 18 wherein said displacement-measurement part uses an optical encoder to sense rotation of said spool.

* * * * *